United States Patent [19]

Robinson

[11] 4,193,399
[45] Mar. 18, 1980

[54] SELF VENTING PLUG FOR VENOUS ENTRY UNIT
[75] Inventor: Thomas P. Robinson, Dallas, Tex.
[73] Assignee: Travenol Laboratories, Inc., Dallas, Tex.
[21] Appl. No.: 813,890
[22] Filed: Jul. 8, 1977
[51] Int. Cl.² .............................................. P61M 5/00
[52] U.S. Cl. .................................. 128/214.4; 55/159; 55/523; 73/425.4 P; 128/348; 128/221
[58] Field of Search ................ 128/214.4, 214 R, 221, 128/DIG. 5, 2 F, 348; 73/425.4 P, 425.6; 23/259; 210/436; 55/178, 159, 523

[56] References Cited

U.S. PATENT DOCUMENTS

| | | | |
|---|---|---|---|
| 3,055,361 | 9/1962 | Ballard | 128/214.4 |
| 3,220,411 | 11/1965 | Czorny | 128/214.4 |
| 3,715,047 | 2/1973 | Sado | 215/261 |
| 3,792,703 | 2/1974 | Moorehead | 128/214.4 |
| 3,864,979 | 2/1975 | Ayres | 73/425.4 P |
| 4,016,879 | 4/1977 | Mellor | 128/214.4 |
| 4,094,303 | 6/1978 | Johnson | 128/1 R |
| 4,106,509 | 8/1978 | McWhorter | 128/349 B |

Primary Examiner—Dalton L. Truluck
Attorney, Agent, or Firm—Richards, Harris, Medlock

[57] ABSTRACT

The specification discloses a self venting plug for a venous entry unit which is a porous plastic body adapted to be removably seated in a hollow flashback chamber. The plug comprises an open pored plastic having a pore size on the order of 10–15 microns, and provides a flow path for venting air from the flashback chamber while inhibiting flow of blood from the chamber. The plug may be used, for example, with over-the-needle and through-the-needle catheter units employing piercing needles, and may be used to anchor a stylet for stiffening a catheter to be forwarded into the body.

11 Claims, 6 Drawing Figures

SELF VENTING PLUG FOR VENOUS ENTRY UNIT

This invention relates to venous entry units, and more particularly relates to a novel and improved plug providing self venting means for the flashback chamber of such units for giving visual indication of vessel entry.

DESCRIPTION OF THE PRIOR ART

In systems employing piercing needles for obtaining entry into the vascular system of the patient, it has long been known to provide a transparent or translucent flashback chamber in fluid communication with the piercing needle. The provision of a chamber permits the nurse or other user of the unit to receive a visual indication of successful vessel entry by observing the flow of blood into the flashback chamber. It has likewise long been known that it is advantageous to provide a means for venting air from the chamber to facilitate the flow of blood into the chamber upon vessel entry. It has been recognized, however, that it is desirable to inhibit the flow of blood outwardly of the chamber for reasons of cleanliness and hygiene as well as to make easier the operator's job in manipulating the device. For this purpose, a number of structures have been utilized in commercial products actually offered in this field, and have been proposed in prior art patents.

One such structure has been to provide a two-position plug for the flashback chamber. In such a system, the unit employing the plug is packaged with the plug positioned in a Luer tapered exit from the hollow flashback chamber in a first position in which gaps are provided by standoff means between the periphery of the plug and the wall of the flashback chamber port. The plug, however, is movable by the operator into a fully seated position that completely seals off the flashback chamber port. With use of such a system, an operator has been expected to move the plug from the first position to the second position once the piercing needle is in the body and vessel entry has been indicated by a flow of blood into the flashback chamber. Such a system has the disadvantage of requiring additional manipulative steps from the operator, whose primary purpose is to obtain entry into the patient's blood vessel and to carry out whatever medical procedure is required at that time. In order to prevent the flow of blood outwardly from the flashback chamber, it is necessary that he move quickly to position the plug in its second position, a movement which may cause additional discomfort to the patient.

Recognizing these disadvantages of a venting system which requires additional manipulation of a plug, structures have been utilized which are passive in the sense that they do not require such additional positioning movements by the operator. For example, U.S. Pat. No. 3,738,381 and U.S. Pat. No. 3,859,998 disclose the use of thin diaphragms such as might be formed from molded plastic extending across the exit of such chambers, such diaphragms being provided with holes or a slit with sufficiently small dimensions to substantially inhibit the flow of blood while permitting venting of air in the chamber.

The assignee of this application has utilized a two-position plug, and more recently has utilized a plug having a thin plastic diaphragm blocking the exit from a hollow flashback chamber in which a small round hole has been pierced. Utilization of this latter system has involved difficulties with providing consistent products having openings of the proper size for the purpose. The manufacture of such products is difficult, since too large a hole may permit the exit of blood, while too small a hole may prevent sufficient venting. Substantial rejects have been found in the formation of such holes.

Finally, one commercial product of which applicant is aware has utilized a closure for the flashback chamber which includes a thin woven material utilized as a diaphragm. This product has been utilized in an Abbocath-T product marketed by Abbott Laboratories.

SUMMARY OF THE INVENTION

By contrast to the long history of prior art attempts to deal with the problem of venting air from flashback chambers, applicant has discovered a structure which is simple to manufacture on a highly reliable basis and which provides a multiplicity of flowpaths of sufficient nature to give a very rapid venting and flashback to quickly ascertain vessel entry while still serving to inhibit the flow of blood from the device.

In accordance with the invention, there is provided a self venting plug seated in the flashback chamber port which comprises a body of porous plastic material having open pores to provide a flowpath for air from the chamber. In a particular aspect, the plastic plug may be a molded polyethylene having a pore size in a preferred range from about 10 to 15 microns. The plug may be utilized in various venous entry systems including, for example, over-the-needle and through-the-needle catheter insertion devices where a piercing needle is used to make vessel entry, and a hollow flashback chamber is provided either on the needle hub or the catheter hub of the device. In through-the-needle catheter forwarding devices where a stiffener or stylet is required for the catheter, the self venting plug may be utilized to anchor the proximal end of the stylet.

DETAILED DESCRIPTION OF THE DRAWINGS

Figure 1:
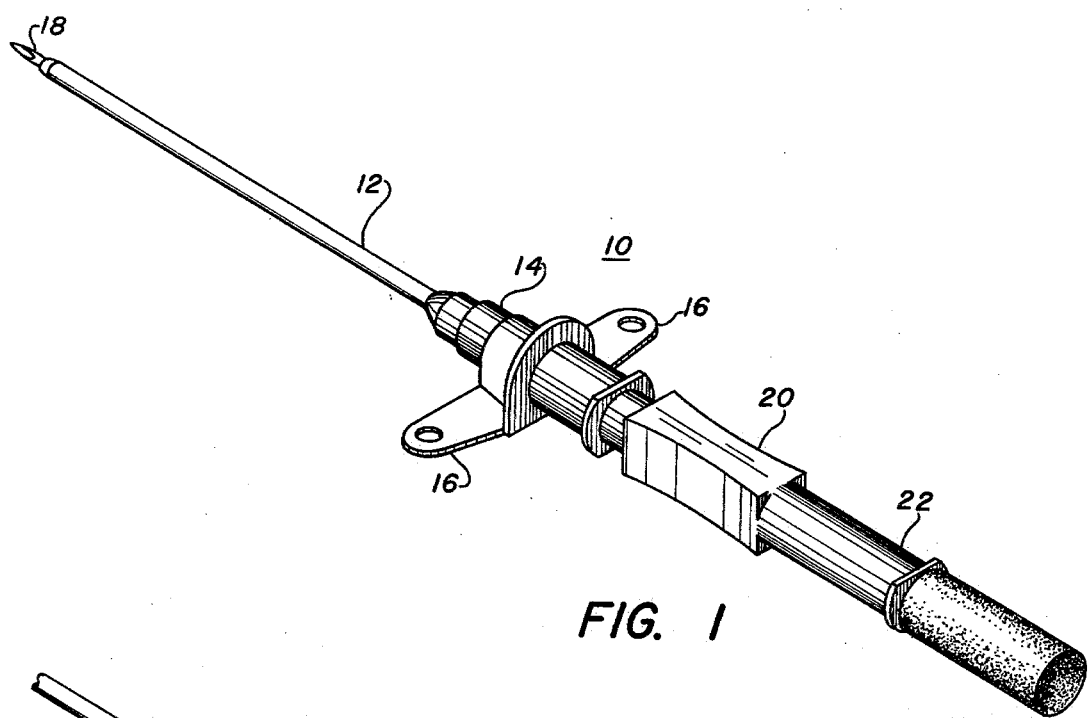
FIG. 1 is a perspective view of a venous entry unit comprising an over-the-needle catheter insertion device which utilizes the present invention.

As illustrated in FIG. 1, the self venting plug of this invention may be utilized in an over-the-needle catheter insertion device, generally indicated by the reference numeral 10. The device 10 typically includes a flexible catheter 12 secured at its proximal end in a plastic catheter hub 14, which may be provided with tie-down wings 16. A piercing needle 18 is removably positioned in the catheter 12 and extends outwardly thereof at the distal end of the catheter. Needle 18 is secured at its proximal end in a needle hub which in this case serves as the flashback chamber 20. Flashback chamber 20 is formed from a transparent or translucent plastic material, so that the flow of blood from the body through the needle into the chamber 20 can be perceived by the user. Flashback chamber 20 is provided with a port section 22 having an internal Luer taper for reception of a syringe or other element for hook-up to the device. The exit port 24 from Luer taper section 22 is, when the device is packaged for use as shown in FIG. 1, closed by a self venting plug 26.

Self venting plug 26 is seated securely but removably in section 22. For this purpose, plug 26 is provided with a male sealing section 28 having a matching Luer taper and a rearward main body portion 30 formed thereon.

Self-venting plug 26 is a plastic body having open pores so that it provides a plurality of flowpaths for venting air through the plug from flashback chamber 20. Plug 26 may conveniently be integrally formed by molding, although other formation techniques such as extrusion, may be utilized.

One material from which plug 26 may satisfactorily be formed is a high molecular weight polyethylene formed with pore size in a preferred range from about 10 to 15 microns. Plugs having pore sizes in this range are preferred, but it is possible that pore sizes in the range of 5 to 25 microns may be useful in some applications. Such a product is provided under the trademark "POREX" by the Porex Materials Corporation as an ultra-high molecular weight polyethylene. Other plastic materials having appropriate pore sizes might also be used.

Figure 2:
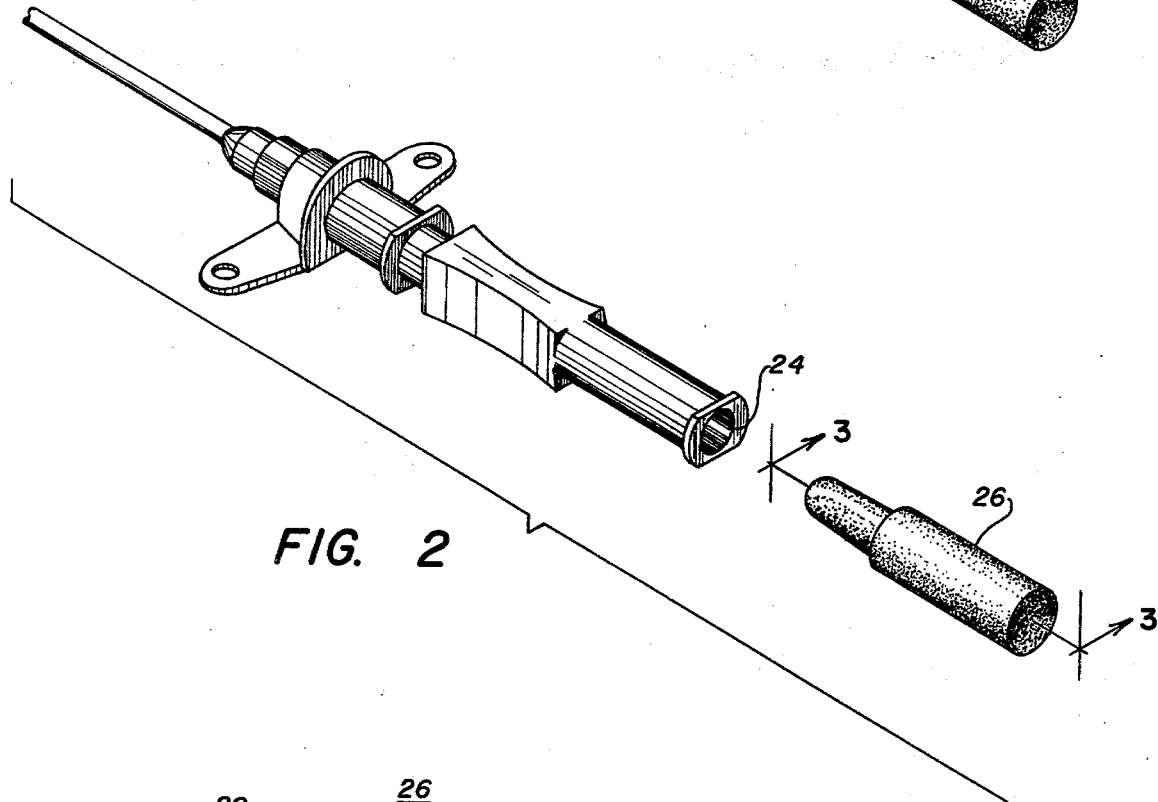
FIG. 2 is a view similar to FIG. 1 with the distal end omitted, and showing the self venting plug removed from its seat in the port of the flashback chamber.
Figure 3:
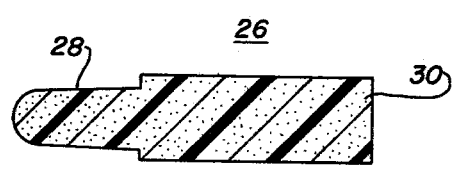
FIG. 3 is a sectional view along the lines 3—3 in FIG. 2 of the self venting plug.

The utilization of the improved self venting plug of this invention in the device illustrated in FIGS. 1 and 2 has a quicker flashback by permitting better venting of the air from the flashback chamber. This is a substantial advantage in the art, since the nurse or other utilizer of a piercing needle vessel entry system needs to know as soon as possible that vessel entry has been obtained. Otherwise, additional and unnecessary probing with the needle may be undertaken and even new entries made when in fact successful entry has been obtained. Thus, the importance of prompt flashback which is facilitated by this system is emphasized. After entry is indicated, the plug 26 may be removed to insert a syringe or other fluid line connector to the Luer section 22.

Figure 4:
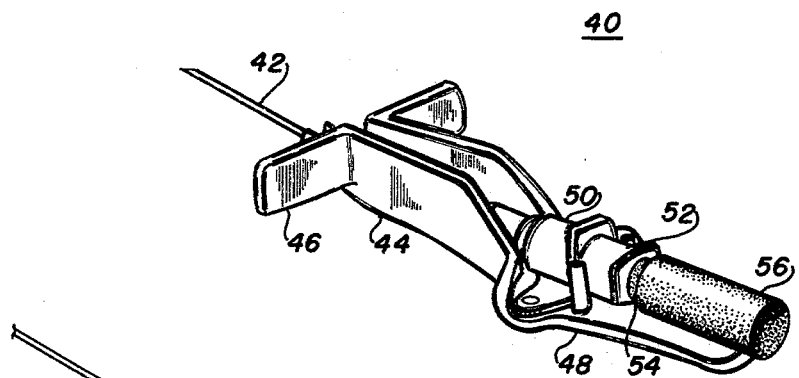
FIG. 4 is a perspective view of a different type of venous entry unit with which the plug may be used, comprising a through-the-slotted-needle catheter insertion device.
Figure 5:
FIG. 5 is a view of the self venting plug of FIG. 4 including a stylet anchored by the plug.
Figure 6:
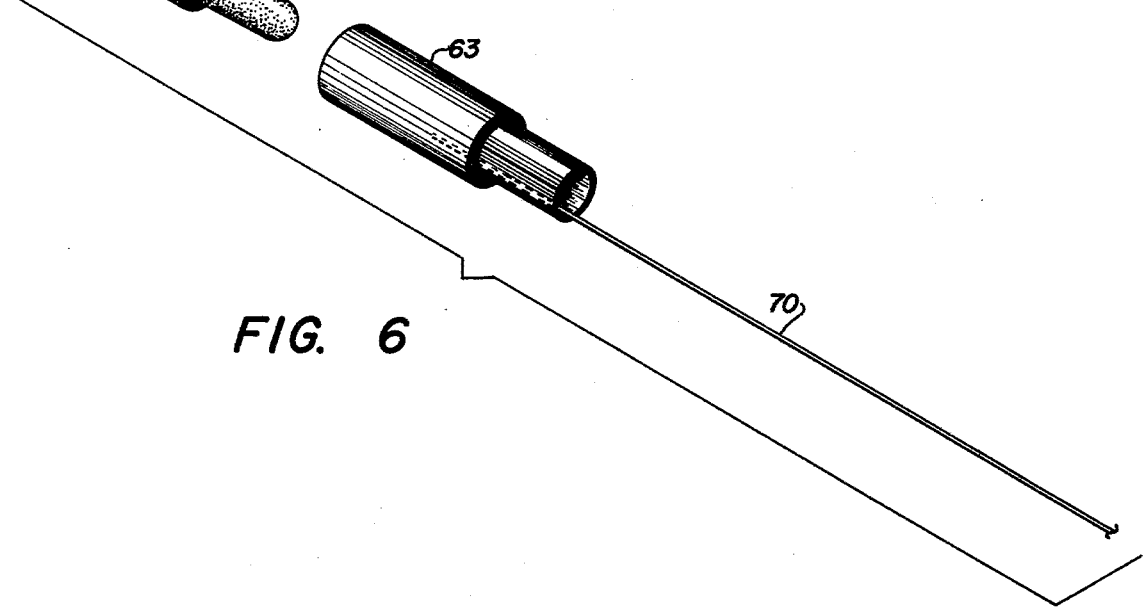
FIG. 6 is a perspective view of a modified form of the self venting plug illustrated in FIG. 5.

FIGS. 4-6 illustrate the utilization of a self-venting plug in accordance with this invention in a venous entry system which comprises a somewhat different form of catheter introduction device. Specifically, FIGS. 4-6 illustrate use of the improved self venting plug of this invention in a through-the-needle catheter introduction device which employs a slotted needle. In devices of this type, generally indicated in FIG. 4 by the reference numeral 40, there is provided a slotted piercing needle 42 secured at its proximal end in a hub 44, which may have handle extensions 46 and a base portion 48 for locking the needle with the corresponding catheter assembly. A catheter (not shown) rests in the hollow of the slotted needle 42, and is secured at its proximal end in a catheter hub 50 which in this case serves as the translucent flashback chamber for ascertaining vessel entry. The flashback chamber 50 is provided with a Luer taper section 52 and an exit port 54 for receipt of syringe or other fluid connection means. The flashback chamber is closed, when the device is packaged for use, by a self venting plug 56 constructed in accordance with this invention. Plug 56 has a distal Luer taper section 58 and a main body portion 60.

In through-the-needle catheter forwarding devices, it is sometimes desirable to have a stiffening means such as a thin wire stylet extending through a catheter during introduction. In this case, the self venting plug 56 may be utililzed to anchor the stylet, indicated by the reference numeral 62. As illustrated in FIG. 5 the stylet 62 may be anchored directly into the distal section 58 of plug 56. Alternatively, as illustrated in FIG. 6, a jacket 63 may be provided with open ends and a hollow body cavity substantially conforming to the external dimensions of a self venting plug 64 having a Luer taper 66 and a main body portion 68. A stylet 70 may be positioned in the jacket 63, and the entire assembly placed together by press-fitting the plug 64 into the jacket 63 and securing the stylet 70 into position. Jacket 63 may be formed by molding a plastic material or from metal by a stamping technique.

In operation, the self venting plug is maintained in position, in any of the embodiments illustrated, until vessel entry has been accomplished. Thereafter, the plug may be removed for such hook-ups and medical procedures as are desired for the particular operation.

Having described the invention in connection with certain specific embodiments thereof, it is to be understood that further modifications may now suggest themselves to those skilled in the art and it is intended to cover such modifications as fall within the scope of the appended claims.

What is claimed is:

1. In a venous entry unit having a hollow needle and a hollow flashback chamber proximal of the needle in fluid communication therewith for obtaining a visual indication of blood vessel entry by flow of blood into the chamber, the chamber having a proximal opening, the improvement comprising:

a self venting plug removably seated in the proximal opening of the flashback chamber and sealingly engaging the inside surface of the flashback chamber adjacent the opening, said plug having as its major portion an integrally formed body of solid porous plastic material with pores therein of predetermined size to provide a flow path for air from the chamber outwardly through the plug while preventing the flow of blood outwardly from said chamber through said plug.

2. The unit of claim 1, wherein the pore size of said porous material is on the order of ten to fifteen microns.

3. The unit of claim 1, wherein said plastic plug is a molded high molecular weight polyethylene having a pore size from about ten to about fifteen microns.

4. The unit of claim 1 wherein the unit is further characterized by the fact that a catheter surrounds the needle and is adapted to be forwarded over the needle into a blood vessel.

5. The unit of claim 1 wherein the unit is further characterized by the fact that a catheter is carried in the hollow needle and is forwardable therethrough.

6. The unit of claim 5 wherein a catheter stylet is positioned in the catheter and is anchored at its proximal end by the self venting plug.

7. The unit of claim 6 wherein the body of porous plastic material is fitted within a jacket which forms the exterior of the plug, and the body extends for substantially the length of the plug.

8. A self venting plug adapted to be removably seated in the tapered opening of a flashback chamber in a venous entry unit, which comprises:

an integral body of porous plastic having open pores therein of predetermined size to provide a flow path through said body for air while inhibiting the flow of blood therethrough from the flashback chamber;

said body having a smoothly tapered forward portion configured for sealing engagement with the interior of said flashback chamber, a relatively enlarged rear portion, and a forwardly facing shoulder portion located between the forward and rear body portions.

9. The plug of claim 7, wherein the plug is a molded polyethylene having a pore size of from about ten to about fifteen microns.

10. The plug of claim 8, wherein the body of porous plastic material is fitted within a jacket which forms the exterior of the plug.

11. In a venous entry unit having a hollow needle and a hollow flashback chamber proximal of the needle in fluid communication therewith for obtaining a visual indication of blood vessel entry by flow of blood into the chamber, the chamber having a proximal opening, the improvement comprising:

an integrally formed porous plastic self venting plug seated in the proximal opening of the flashback chamber and engaging the inside surface of the flashback chamber adjacent the opening, said plug having open pores therein of predetermined size to provide flow path for air from the chamber outwardly through the plug while preventing the flow of blood therethrough and having a smooth distal portion for sealingly engaging the inside surface of the flashback chamber.

* * * * *

UNITED STATES PATENT AND TRADEMARK OFFICE
CERTIFICATE OF CORRECTION

PATENT NO. : 4,193,399
DATED : March 18, 1980
INVENTOR(S) : Thomas P. Robinson

It is certified that error appears in the above—identified patent and that said Letters Patent is hereby corrected as shown below:

Column 5, line 9, change "7" to --8--.

Signed and Sealed this

Fourth Day of December 1984

[SEAL]

Attest:

*Attesting Officer*

GERALD J. MOSSINGHOFF

*Commissioner of Patents and Trademarks*